(12) United States Patent
Murata et al.

(10) Patent No.: US 8,697,899 B2
(45) Date of Patent: Apr. 15, 2014

(54) METHODS FOR PRODUCING IRON METHACRYLATE AND HYDROXYALKYL METHACRYLATE

(75) Inventors: Naoshi Murata, Hiroshima (JP); Kuniyoshi Ogura, Hiroshima (JP); Takeshi Matsuo, Hiroshima (JP); Akira Yoshioka, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 13/822,017

(22) PCT Filed: Dec. 26, 2011

(86) PCT No.: PCT/JP2011/080011
§ 371 (c)(1),
(2), (4) Date: Mar. 11, 2013

(87) PCT Pub. No.: WO2012/090905
PCT Pub. Date: May 7, 2012

(65) Prior Publication Data
US 2013/0172591 A1　Jul. 4, 2013

(30) Foreign Application Priority Data

Dec. 27, 2010　(JP) ................. 2010-290879

(51) Int. Cl.
*C07F 15/00*　(2006.01)
*C07C 67/26*　(2006.01)

(52) U.S. Cl.
USPC ............................ 556/149; 560/209

(58) Field of Classification Search
USPC ........................... 556/149; 560/209
See application file for complete search history.

(56) References Cited

FOREIGN PATENT DOCUMENTS

| JP | 57 175141 | 10/1982 |
|---|---|---|
| JP | 7 17896 | 1/1995 |
| JP | 2008 201780 | 9/2008 |
| JP | 2010 023953 | 3/2010 |

*Primary Examiner* — Porfirio Nazario Gonzalez
(74) *Attorney, Agent, or Firm* — Oblon, Spivak, McClelland, Maier & Neustadt, L.L.P.

(57) ABSTRACT

There is provided a method for producing iron methacrylate being inexpensive, and being high in activity and selectivity and good in solubility to a reaction liquid when being used in production of a hydroxyalkyl methacrylate as a catalyst. The method for producing iron methacrylate for production of a hydroxyalkyl methacrylate according to the present invention includes subjecting a mixture of a metallic iron having an oxygen atom content by XRF analysis of the surface thereof of 6% by mass or lower, and methacrylic acid to a heat treatment at 95° C. or higher and lower than 110° C. for 100 to 600 min. The method for producing a hydroxyalkyl methacrylate according to the present invention includes reacting an alkylene oxide with methacrylic acid to produce the hydroxyalkyl methacrylate, wherein iron methacrylate produced by the method according to the present invention is used as a catalyst.

20 Claims, No Drawings

METHODS FOR PRODUCING IRON METHACRYLATE AND HYDROXYALKYL METHACRYLATE

TECHNICAL FIELD

The present invention relates to methods for producing iron methacrylate and a hydroxyalkyl methacrylate.

BACKGROUND ART

Several methods for producing iron methacrylate have been proposed.

For example, a method has been proposed, in which methacrylic acid, an alkaline metal and an iron salt such as iron nitrate are mixed in a solvent such as water, and iron methacrylate is produced by salt exchange (Patent Literature 1). Since this method has a difficulty in securely completing salt exchange, iron methacrylate is difficult to obtain in a high yield of 90% or higher. The method has further problems such as a reduction in purity due to contamination of iron methacrylate with impurities derived from nitric acid, and a rise in the cost because of necessity of filtration and drying processes. In the case where a hydroxyalkyl methacrylate is produced by using the prepared iron methacrylate as a catalyst, there are concern about problems, such as by-production of impurities, coloration and the like derived from nitric acid contained in the catalyst raw material.

Other methods include a method in which a metallic iron is dissolved in methacrylic acid (Patent Literatures 2 and 3). Since iron methacrylate prepared by this method is obtained as a solution of methacrylic acid containing iron methacrylate, the solution is suitable because the solution can be used as it is for production of a hydroxyalkyl methacrylate by using the iron methacrylate as a catalyst and the methacrylic acid as a raw material. That is, since filtration and drying processes and the like are not needed, the production cost can be reduced. A high-quality hydroxyalkyl methacrylate which contains no impurities derived from halogens, and exhibits little coloration can be produced.

CITATION LIST

Patent Literature

Patent Literature 1: JP07-17896A
Patent Literature 2: JP57-175141A
Patent Literature 3: JP2008-201780A

SUMMARY OF INVENTION

Technical Problem

The latter method in which a metallic iron is dissolved in methacrylic acid to produce iron methacrylate can prevent contamination with impurities derived from nitric acid better and can produce iron methacrylate at a lower cost than the former method in which iron nitrate and the like are used as raw materials. However, heating is needed in order to dissolve a metallic iron in methacrylic acid, and it has been proved that, depending on heating temperature and heating time, the methacrylic acid polymerizes during dissolution, and the catalyst performance decreases.

It has been proven that in the case where iron methacrylate produced by heating and dissolving a metallic iron in methacrylic acid by a conventional method is used as a catalyst for synthesis of a hydroxyalkyl methacrylate, there arises a large variation in the catalyst performance because the oxygen atom content of the surface of the metallic iron and the condition in the preparation of the catalyst are not suitable. Herein, the catalyst performance refers to the activity and the selectivity of a catalyst, and the solubility of the catalyst in a reaction liquid in this specification. The solubility of a catalyst refers to a degree of homogeneous dissolution of the catalyst in a reaction liquid from during the reaction to after the reaction; and "solubility is good" indicates a situation in which the reaction liquid contains no deposit and is a homogeneous transparent liquid. If the catalyst is a catalyst homogeneously dissolving in a reaction liquid, no trouble occurs such as the solidification thereof in the distillation operation after the reaction and the clogging of the deposited catalyst in a distillation apparatus. Therefore, a good solubility is important from the viewpoint of being suitable for industrial distillation refining.

The present invention has an object to provide a method for producing iron methacrylate which is inexpensive, and has a high activity and selectivity, and exhibits a good solubility in a reaction liquid when used as a catalyst in the production of a hydroxyalkyl methacrylate.

Solution to Problem

The method for producing iron methacrylate for production of a hydroxyalkyl methacrylate according to the present invention includes subjecting a mixture of a metallic iron having an oxygen atom content by XRF analysis of the surface thereof of 6% by mass or lower, and methacrylic acid to a heat treatment at 95° C. or higher and lower than 110° C. for 100 to 600 min.

Advantageous Effects of Invention

The present invention can provide a method for producing iron methacrylate which is inexpensive, and has a high activity and selectivity, and exhibits a good solubility in a reaction liquid when used as a catalyst in production of a hydroxyalkyl methacrylate.

DESCRIPTION OF EMBODIMENTS

In the present invention, there have been studied in detail the oxygen atom content of the surface of a metallic iron and the reaction condition of the metallic iron with methacrylic acid in production of iron methacrylate for production of a hydroxyalkyl methacrylate (hereinafter, also referred to as "iron methacrylate" simply). As a result, the production condition under which the catalyst performance is made optimum when the iron methacrylate is used as a catalyst for production of a hydroxyalkyl methacrylate has been found. It has also been found that in addition to iron methacrylate as a catalyst, a quaternary ammonium salt and an amine compound can be added. The optimum ratio of catalyst components has been further found. Hereinafter, an embodiment according to the present invention will be described.

[Method for Producing Iron Methacrylate]

The method for producing iron methacrylate according to the present invention includes subjecting a mixture of a metallic iron having an oxygen atom content by XRF analysis of the surface thereof of 6% by mass or lower and methacrylic acid to a heat treatment at 95° C. or higher and lower than 110° C. for 100 to 600 min.

The shape of a metallic iron as a raw material of iron methacrylate relevant to the present invention is not especially limited, but is preferably a powdery iron (iron powder)

from the viewpoint of solubility. The particle diameter of the iron powder is not especially limited, but is preferably 10 to 500 μm, and more preferably 60 to 300 μm from the viewpoint of solubility and safety. The kind of the iron powder is not especially limited, but includes, for example, atomized iron powder, reduced iron powder and electrolytic iron powder. Atomized iron powder and reduced iron powder are preferable from the viewpoint of the cost. These metallic irons may be used singly or concurrently in two or more.

The oxygen atom content of the surface of a metallic iron by XRF analysis is 6% by mass or lower.

XRF analysis refers to X-ray fluorescence analysis, and usual devices can be used.

The surface of a metallic iron is oxidized with oxygen in the air, and a film of iron oxide is formed. Since the oxide film affects the solubility of iron, the oxygen atom content of the surface needs to be in a specific range. Since the solubility of the metallic iron to methacrylic acid decreases when the oxygen atom content of a metallic iron surface by XRF analysis is too high, the oxygen atom content is made to be 6% by mass or lower. In order to secure good solubility, the oxygen atom content of a metallic iron surface is preferably 3% by mass or lower. The lower limit of the oxygen atom content of a metallic iron surface is preferably higher than 0% by mass, more preferably 1% by mass or higher, and still more preferably 1.5% by mass or higher, from the viewpoint of the solubility of the metallic iron.

Metallic irons having various values of the oxygen atom contents of the surfaces of the metallic irons are commercially available. The oxygen atom amount of a metallic iron surface may be regulated by reduction treatment and oxidation treatment.

The reduction treatment usually involves contact treatment of a reducing agent with a metallic iron. Well-known reducing agents such as carbon and hydrogen can be used as the reducing agent; the reduction reaction proceeds by heating, for example, carbon such as charcoal, and a metallic iron at a high temperature of 400° C. or higher.

The oxidation treatment usually involves contact treatment of an oxidizing agent with a metallic iron. The oxidizing agent is generally oxygen in the air. Since the oxidation is promoted in an acidic aqueous solution, the oxidation reaction proceeds, for example, by a method of introducing the air in an acidic aqueous solution while dispersing and stirring a metallic iron in the acidic aqueous solution.

The heating temperature when a mixture of a metallic iron and methacrylic acid is subjected to a heat treatment is 95° C. or higher and lower than 110° C. Since the temperature at which the dissolution of the metallic iron starts is 95° C. or higher, the metallic iron does not sufficiently dissolve when the heating temperature is lower than 95° C. When the heating temperature is 110° C. or higher, on the other hand, the catalyst performance (activity, selectivity, solubility) decreases, and the possibility that methacrylic acid polymerizes rises, which are not preferable. The heating temperature is preferably 95° C. or higher and 105° C. or lower, and the heat treatment is more preferably carried out in a lowest temperature range in which the metallic iron dissolves in the above-mentioned range.

When a mixture of a metallic iron and methacrylic acid is subjected to the heat treatment, the heat treatment is carried out at 95° C. or higher and lower than 110° C. for 100 to 600 min. The case where the mixture is heated in the above temperature range for less than 100 min is not preferable because the metallic iron does not sufficiently dissolve. In the case of being heated in the above temperature range for more than 600 min, on the other hand, the catalyst performance decreases and the polymerization of methacrylic acid occurs, which are not preferable. A heat treatment of the mixture at 95° C. or higher and lower than 110° C. is preferably carried out for 150 to 500 min, and more preferably 200 to 400 min.

In the method according to the present invention, since it takes a long time to dissolve all metallic iron to thereby reduce the productivity of the catalyst production when the amount of the metallic iron is large, the temperature may be raised higher. In this case, it is preferable that a heat treatment is carried out at 95° C. or higher and lower than 110° C. for 100 to 600 min, and thereafter, a heat treatment is carried out at 110° C. or higher and 125° C. or lower for 30 to 300 min, and the temperature is lowered to 100° C. or lower. The selectivity is improved by holding the temperature at 95° C. or higher and lower than 110° C. for 100 min or more, and thereafter raising the temperature to 110° C. or higher. The increase in temperature to 125° C. or lower does not cause a decrease in the selectivity and the polymerization. Holding the temperature at 95° C. or higher and lower than 110° C. for 600 min or less, and thereafter raising the temperature and heating at 110° C. or higher and 125° C. or lower for 300 min or less does not cause a decrease in the selectivity, a decrease in the catalyst performance such as occurrence of deposits, and the polymerization. It is more preferable that a heat treatment is carried out at 95° C. or higher and lower than 110° C. for 100 to 600 min, and thereafter, a heat treatment is carried out at 110° C. or higher and 120° C. or lower for 100 to 150 min, and the temperature is lowered to 100° C. or lower. It is still more preferable that a heat treatment is carried out at 95° C. or higher and lower than 110° C. for 200 to 250 min, and thereafter, a heat treatment is carried out at 110° C. or higher and 120° C. or lower for 100 to 150 min, and the temperature is lowered to 100° C. or lower.

The moisture amount in methacrylic acid used in the method according to the present invention is preferably 300 ppm or smaller. Making the moisture amount in methacrylic acid to be 300 ppm or smaller can suppress the formation of iron hydroxide during the heat treatment of a mixture of a metallic iron and methacrylic acid and can prevent a decrease in the catalyst activity and the catalyst deposition. Making the moisture amount in methacrylic acid to be 300 ppm or smaller can be achieved by well-known methods including refining by distillation, and use of a dehydrating agent, and later storage in a closed container. The moisture amount in methacrylic acid is more preferably 200 ppm or smaller.

When a mixture of a metallic iron and methacrylic acid is subjected to a heat treatment, it is preferable to blow in an oxygen-containing gas such as oxygen or the air for inhibiting polymerization. It is also preferable that a polymerization inhibitor is added to the mixture and the heat treatment is carried out in the coexistence of the polymerization inhibitor. The polymerization inhibitor includes, for example, phenolic compounds such as hydroquinone and paramethoxyphenol, amine-based compounds such as N,N'-diisopropylparaphenylenediamine, N,N'-di-2-naphthylparaphenylenediamine, N-phenyl-N-(1,3-dimethylbutyl)paraphenylenediamine and phenothiazine, N-oxyl-based compounds such as 4-hydroxy-2,2,6,6-tetramethylpiperidine-N-oxyl and 4-benzoyloxy-2,2,6,6-tetramethylpiperidine-N-oxyl, and N-oxyl-based compounds exemplified by the following formula (1).

[Formula 1]

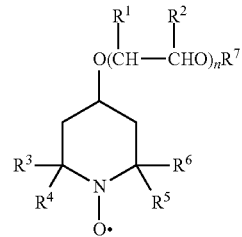

(1)

wherein n=1 to 18; $R^1$ and $R^2$ are both H, or one of $R^1$ and $R^2$ is a hydrogen atom, and the other is a methyl group; $R^3$, $R^4$, $R^5$ and $R^6$ are each a linear or branched alkyl group; and $R^7$ is H or a (meth)acryloyl group. These polymerization inhibitors may be used singly or concurrently in two or more.

Iron methacrylate prepared in such a way can be used preferably as a catalyst for production of a hydroxyalkyl methacrylate.

[Method for Producing a Hydroxyalkyl Methacrylate]

In the method according to the present invention, a hydroxyalkyl methacrylate is produced by an addition reaction of methacrylic acid and an alkylene oxide.

The alkylene oxide includes alkylene oxides having 2 to 6 carbon atoms. The alkylene oxide specifically includes ethylene oxide, propylene oxide and butylene oxide. A hydroxyalkyl methacrylate produced by the method according to the present invention includes, for example, hydroxyethyl methacrylate and hydroxypropyl methacrylate.

A method for producing methacrylic acid as a raw material is not especially limited, and methacrylic acid produced by a well-known method such as the C4 oxidation method or the ACH method can be used. A method for producing an alkylene oxide is not especially limited also, and an alkylene oxide produced by a well-known method such as the ring-closure reaction of a halohydrin or the oxidation reaction of an olefin can be used.

In the method according to the present invention, iron methacrylate produced by the method according to the present invention is used as a catalyst. The iron methacrylate can be used as a catalyst in the state of a methacrylic acid solution containing iron methacrylate (hereinafter, referred to as an iron methacrylate-containing methacrylic acid solution), and exhibits a high activity, a high selectivity and a high solubility to a reaction liquid.

In the method according to the present invention, it is preferable from the viewpoint of the improvement in the activity and the selectivity to further use a quaternary ammonium salt and an amine compound in addition to iron methacrylate produced by the method according to the present invention as catalysts.

The quaternary ammonium salt is not especially limited, but is preferably a tetraalkylammonium salt from the viewpoint of good properties of residues from distillation and the reduction in coloration of a distillate. The alkyl group of the tetraalkylammonium salt may be linear or branched, and may be one to which a substituent such as a hydroxyl group or a phenyl group is further attached. A tetraalkylammonium salt usable is, for example, a compound represented by the following formula (2).

$$N^+(R^8)(R^9)(R^{10})(R^{11})X^- \qquad (2)$$

wherein $R^8$ to $R^{11}$ each denote a substituted or unsubstituted linear or branched alkyl group or a phenyl group; and X denotes a halogen or OH.

In the above formula (2), a substituent of the alkyl group of $R^8$ to $R^{11}$ includes a hydroxyl group and a phenyl group. The longer the alkyl group of $R^8$ to $R^{11}$, the more the activity is improved, which is preferable; and a butyl group, which has 4 carbon atoms, is preferable from the viewpoint of economic efficiency. The tetraalkylammonium salt includes, for example, a tetramethylammonium salt, a triethylbenzylammonium salt, a phenyltrimethylammonium salt, a tetrabutylammonium salt, a tetraoctylammonium salt and a choline salt. The halogen of X includes chlorine, bromine and iodine. These may be used singly or concurrently in two or more.

The amine compound is not especially limited, but preferably a tertiary amine from the viewpoint of the reduction of coloration of products and the economic efficiency. The tertiary amine is preferably a trialkylamine. The alkyl group of the trialkylamine may be linear or branched, and may be one to which a substituent such as a hydroxyl group or a phenyl group is further attached. A tertiary amine usable is, for example, a compound represented by the following formula (3).

$$N(R^{12})(R^{13})(R^{14}) \qquad (3)$$

wherein $R^{12}$ to $R^{14}$ each denote a substituted or unsubstituted linear or branched alkyl group or a phenyl group.

In the above formula (3), a substituent of the alkyl group of $R^{12}$ and $R^{14}$ includes a hydroxyl group and a phenyl group. The tertiary amine includes, for example, trimethylamine, triethylamine, triethanolamine (TEOA) and tributylamine. These may be used singly or concurrently in two or more. It is preferable also from the viewpoint of being capable of suppressing by-production of alkylene dimethacrylates and dialkylene glycol monomethacrylates that an amine compound is added as a catalyst.

The use amount of a quaternary ammonium salt is preferably 0.5 to 1.5 mol with respect to 1 mol of iron methacrylate. Use of 0.5 to 1.5 mol of a quaternary ammonium salt with respect to 1 mol of iron methacrylate can improve the selectivity. A quaternary ammonium salt is more preferably used in 0.7 to 1.3 mol, and still more preferably in 0.8 to 1.2 mol, with respect to 1 mol of iron methacrylate. Some cases where the use amount of a quaternary ammonium salt is 2.0 mol or larger with respect to 1 mol of iron methacrylate reduce the selectivity.

The use amount of an amine compound is preferably 0.5 to 5.0 mol with respect to 1 mol of iron methacrylate. Use of 0.5 mol or more of an amine compound with respect to 1 mol of iron methacrylate improves the selectivity. Use of 5.0 mol or less of an amine compound with respect to 1 mol of iron methacrylate can improve the selectivity without raising the cost. An amine compound is used more preferably in 0.7 to 2.0 mol, and still more preferably in 0.8 to 1.5 mol, with respect to 1 mol of iron methacrylate.

The feed ratio of raw materials is not especially limited, but the molecular ratio of methacrylic acid and an alkylene oxide (methacrylic acid/alkylene oxide) is preferably 0.1 or higher and 10 or lower, and more preferably 0.5 or higher and 2 or lower, from the viewpoint of the productivity. The addition amount of iron methacrylate as a catalyst is not especially limited, but is preferably 0.01 mol % or higher and 10 mol % or lower, and more preferably 0.1 mol % or higher and 5 mol % or lower, with respect to a raw material of a smaller feed amount (mol) out of the methacrylic acid and the alkylene oxide, from the viewpoint of a balance between the reaction speed and the economic efficiency. The reaction temperature is preferably 0° C. or higher and 150° C. or lower, and more preferably 30° C. or higher and 100° C. or lower, from the viewpoint of the reaction speed and the suppression of the side reaction. The reaction is preferably carried out in the coexistence of a polymerization inhibitor, and a well-known polymerization inhibitor can be used. For example, a polymerization inhibitor exemplified in the above-mentioned method for producing iron methacrylate can be used. A refining method after the reaction is not especially limited, but includes, for example, distillation. The distillation includes, for example, thin-film distillation.

EXAMPLES

Hereinafter, the present invention will be described in detail by way of Examples, but the present invention is not limited thereto. The analysis of products in Examples was carried out using gas chromatography (GC). The X-ray fluorescence analysis (XRF analysis) was carried out in the mode of SQX qualitative analysis using an X-ray fluorescence analyzer, ZSX100e, made by Rigaku Corp.

Example 1-1

(Preparation of an Iron Methacrylate-Containing Methacrylic Acid Solution)

1.005 g (0.018 mol) of an iron powder (electrolytic iron powder, made by Wako Pure Chemical Industries, Ltd., 100 mesh (150 μm)) having an oxygen atom content by XRF analysis of the surface thereof of 2.1% by mass, 0.03 g of hydroquinone (HQ), and 450 g (5.23 mol) of methacrylic acid (MAA) containing a moisture amount of 151 ppm were fed in a 1-L four-necked flask equipped with a cooling tube, a thermometer and an air introduction tube. The solution was heated and stirred under bubbling thereof with the air at a flow rate of 10 ml/min. The internal temperature became 100° C. at 4 min after reached 95° C., and was held at 100° C. for 300 min; thereby, the iron powder completely dissolved and the solution turned to be a homogeneous red one, and was then allowed to cool. An iron methacrylate-containing methacrylic acid solution was thus prepared.

The yield of iron methacrylate in an iron methacrylate-containing methacrylic acid solution separately prepared in the same way was 95.6%.

(Synthesis of Hydroxyethyl Methacrylate)

A mixed solution of the entire amount of the prepared iron methacrylate-containing methacrylic acid solution, 2.512 g (0.018 mol) of choline chloride and 0.839 g (0.0466 mol) of water, and a solution in which 2.6856 g (0.018 mol) of triethanolamine (TEOA) and 0.053 g of a benzyl ester of HO-TEMPO as a polymerization inhibitor were dissolved in 61 g (0.71 mol) of methacrylic acid (MAA) were fed in a 1-L SUS-made autoclave. 29.1 g (0.661 mol) of ethylene oxide (EO) was dropped thereto at 30° C. over 7 min. Then, 280.9 g (6.377 mol) of ethylene oxide (EO) was dropped thereto at 66° C. over 120 min. Then, the reaction liquid was matured at 66° C. for 4 hours. Thereafter, ethylene oxide (EO) remaining in the reaction liquid was removed at 51° C. at a reduced pressure of 11.325 kPa for 1.5 hours. The reaction liquid was analyzed by GC. The reaction yield of hydroxyethyl methacrylate was 89.5% (based on methacrylic acid). The amount of remaining methacrylic acid was 1.06%; the amount of by-produced ethylene glycol dimethacrylate was 0.07%; and the amount of diethylene glycol monomethacrylate was 4.10%. No deposition of solid materials in the reaction liquid was observed at all.

Example 1-2

(Preparation of an Iron Methacrylate-Containing Methacrylic Acid Solution)

An iron methacrylate-containing methacrylic acid solution was prepared as in Example 1-1, except for altering the holding time of 300 min to 480 min. The yield of iron methacrylate in an iron methacrylate-containing methacrylic acid solution separately prepared in the same way was 95.6%.

(Synthesis of Hydroxyethyl Methacrylate)

Hydroxyethyl methacrylate was synthesized as in Example 1-1, except for using the iron methacrylate-containing methacrylic acid solution of Example 1-2. The reaction yield of hydroxyethyl methacrylate was 89.3% (based on methacrylic acid). The amount of remaining methacrylic acid was 1.01%; the amount of by-produced ethylene glycol dimethacrylate was 0.05%; and the amount of diethylene glycol mono(meth)acrylate was 3.83%. No deposition of solid materials in the reaction liquid was observed at all.

Example 2

(Preparation of an Iron Methacrylate-Containing Methacrylic Acid Solution)

0.9549 g (0.0171 mol) of an iron powder (electrolytic iron powder, made by Wako Pure Chemical Industries, Ltd., 100 mesh (150 μm)) having an oxygen atom content by XRF analysis of the surface thereof of 2.1% by mass, 0.03 g of hydroquinone (HQ), and 385 g (4.48 mol) of methacrylic acid (MAA) containing a moisture amount of 151 ppm were fed in a 1-L four-necked flask equipped with a cooling tube, a thermometer and an air introduction tube. The solution was heated and stirred under bubbling thereof with the air at a flow rate of 10 ml/min. The internal temperature became 100° C. at 9 min after reached 95° C., and was held at 100° C. for 180 min. The internal temperature was thereafter raised to 110° C. over 22 min, and held at 110° C. for 30 min. The internal temperature was thereafter further raised to 120° C. over 16 min, and held at 120° C. for 60 min. At this time, the iron powder completely dissolved and the solution turned to be a homogeneous red one, and was then allowed to cool to 110° C. or lower over 10 min, and thereafter allowed to cool to 100° C. or lower over 12 min (22 min in total).

(Synthesis of Hydroxyethyl Methacrylate)

A mixed solution of the entire amount of the prepared iron methacrylate-containing methacrylic acid solution, 2.6376 g (0.0189 mol) of choline chloride and 0.879 g (0.0488 mol) of water, and a solution in which 2.9243 g (0.0196 mol) of triethanolamine (TEOA) and 0.053 g of a benzyl ester of HO-TEMPO as a polymerization inhibitor were dissolved in 126 g (1.47 mol) of methacrylic acid (MAA) were fed in a 1-L SUS-made autoclave. 29.3 g (0.665 mol) of ethylene oxide (EO) was dropped thereto at 30° C. over 7 min. Then, 305.7 g (6.940 mol) of ethylene oxide (EO) was dropped thereto at 66° C. over 120 min. Then, the reaction liquid was matured at 66° C. for 4 hours. Thereafter, ethylene oxide (EO) remaining in the reaction liquid was removed at 51° C. at a reduced pressure of 11.325 kPa for 1.5 hours. The reaction liquid was analyzed by GC. The reaction yield of hydroxyethyl methacrylate was 90.0% (based on methacrylic acid). The amount of remaining methacrylic acid was 0.79%; the amount of by-produced ethylene glycol dimethacrylate was 0.08%; and the amount of diethylene glycol monomethacrylate was 3.83%. No deposition of solid materials in the reaction liquid was observed at all.

Examples 3 to 11, and Comparative Examples 1 to 6

Iron methacrylate-containing methacrylic acid solutions were prepared, and syntheses of hydroxyethyl methacrylate were carried out as in Examples 1 and 2, except for using iron powders and conditions shown in Tables 1 to 4.

Here, iron powders used in Examples 6 and 7 were an atomized iron powder (made by Wako Pure Chemical Industries, Ltd., particle diameter: 180 μm) having an oxygen atom content by XRF analysis of the surface thereof of 2.1% by mass. In the preparation of the iron methacrylate-containing methacrylic acid solutions in all the Examples and all the Comparative Examples, the iron methacrylate-containing methacrylic acid solutions were finally cooled to 100° C. or lower. In all the Examples and all the Comparative Examples, the total amount of methacrylic acid used in both of the preparation of an iron methacrylate-containing methacrylic acid solution and the synthesis of hydroxyethyl methacrylate was made to be 511 g (5.94 mol). The addition method (temperature, feed rate, feed time) of ethylene oxide was in the same way as the case in Examples 1 and 2, but there were slight differences in feed rate of a pump among each Example and Comparative Example, resulting in that different amounts of ethylene oxide were fed. Therefore, in Table 4, the amounts of ethylene oxide actually fed are shown.

Examples 12 to 15, and Comparative Examples 7 and 8

Iron methacrylate-containing methacrylic acid solutions were prepared using various iron powders, as in Example 2, and evaluated for their solubility, which are shown in Table 5. The solubility was checked by using the holding time from a time when 120° C. was reached after the heating to 120° C. in the same way as the case in Example 2 was carried out.

TABLE 1

| | Preparation of Catalyst | | | | | | | | |
|---|---|---|---|---|---|---|---|---|---|
| | Iron Powder | | MAA | | Moisture Content in MMA | Preparation Temperature | Preparation Time | Preparation Temperature Range | Preparation Time |
| Example | (g) | (mol) | (g) | (mol) | (ppm) | (° C.) | (min) | (° C.) | (min) |
| 1-1 | 1.005 | 0.018 | 450 | 5.23 | 151 | 95→100 | 4 | 95 to <110 | 304 |
| | | | | | | 100 | 300 | | |
| 1-2 | 1.005 | 0.018 | 450 | 5.23 | 151 | 95→100 | 4 | 95 to <110 | 484 |
| | | | | | | 100 | 480 | | |
| 2 | 0.9549 | 0.0171 | 385 | 4.48 | 151 | 95→100 | 9 | 95 to <110 | 211 |
| | | | | | | 100 | 180 | | |
| | | | | | | 100→110 | 22 | | |
| | | | | | | 110 | 30 | 110-125 | 116 |
| | | | | | | 110→120 | 16 | | |
| | | | | | | 120 | 60 | | |
| | | | | | | 120→110 | 10 | | |
| 3 | 1.005 | 0.018 | 450 | 5.23 | 151 | 95→100 | 10 | 95 to <110 | 212 |
| | | | | | | 100 | 180 | | |
| | | | | | | 100→110 | 22 | | |
| | | | | | | 110 | 30 | 110-125 | 115 |
| | | | | | | 110→120 | 16 | | |
| | | | | | | 120 | 60 | | |
| | | | | | | 120→110 | 9 | | |
| 4 | 1.005 | 0.018 | 450 | 5.23 | 151 | 95→100 | 10 | 95 to <110 | 213 |
| | | | | | | 100 | 180 | | |
| | | | | | | 100→110 | 12 | | |
| | | | | | | 110 | 120 | 110-125 | 120 |
| 5 | 1.117 | 0.020 | 450 | 5.23 | 151 | 95→100 | 9 | 95 to <110 | 210 |
| | | | | | | 100 | 180 | | |
| | | | | | | 100→110 | 21 | | |
| | | | | | | 110 | 30 | 110-125 | 117 |
| | | | | | | 110→120 | 17 | | |
| | | | | | | 120 | 60 | | |
| | | | | | | 120→110 | 10 | | |

| | Preparation of Catalyst | | | |
|---|---|---|---|---|
| | Additive | | Molar Ratio, Choline Chloride/Iron | |
| Example | Kind | (mol) | (mol/mol) | Remarks |
| 1-1 | TEOA | 0.018 | 1.0 | Homogeneous dissolution |
| | MAA | 0.71 | | |
| | Choline chloride | 0.018 | | |
| | Water | 0.0466 | | |
| 1-2 | TEOA | 0.018 | 1.0 | Homogeneous dissolution |
| | MAA | 0.71 | | |
| | Choline chloride | 0.018 | | |
| | Water | 0.0466 | | |
| 2 | TEOA | 0.0196 | 1.1 | Homogeneous dissolution |
| | MAA | 1.47 | | |
| | Choline chloride | 0.0189 | | |
| | Water | 0.0488 | | |
| 3 | TEOA | 0.018 | 1.0 | Homogeneous dissolution |
| | MAA | 0.71 | | |
| | Choline chloride | 0.018 | | |
| | Water | 0.0466 | | |
| 4 | TEOA | 0.018 | 1.0 | Homogeneous dissolution |
| | MAA | 0.71 | | |
| | Choline chloride | 0.018 | | |
| | Water | 0.0466 | | |
| 5 | TEOA | 0.010 | 1.0 | Homogeneous dissolution |
| | MAA | 0.71 | | |

TABLE 1-continued

| | | |
|---|---|---|
| | Choline chloride | 0.020 |
| | Water | 0.0517 |

TABLE 2

| | Preparation of Catalyst | | | | | | | | |
|---|---|---|---|---|---|---|---|---|---|
| | Iron Powder | | MAA | | Moisture Content in MMA | Preparation Temperature | Preparation Time | Preparation Temperature Range | Preparation Time |
| Example | (g) | (mol) | (g) | (mol) | (ppm) | (° C.) | (min) | (° C.) | (min) |
| 6 | 1.005*) | 0.018 | 450 | 5.23 | 151 | 95→100 | 9 | 95 to <110 | 211 |
| | | | | | | 100 | 180 | | |
| | | | | | | 100→110 | 22 | | |
| | | | | | | 110 | 30 | 110-125 | 116 |
| | | | | | | 110→120 | 16 | | |
| | | | | | | 120 | 60 | | |
| | | | | | | 120→110 | 10 | | |
| 7 | 1.005*) | 0.018 | 450 | 5.23 | 151 | 95→100 | 11 | 95 to <110 | 212 |
| | | | | | | 100 | 180 | | |
| | | | | | | 100→110 | 21 | | |
| | | | | | | 110 | 30 | 110-125 | 143 |
| | | | | | | 110→120 | 14 | | |
| | | | | | | 120 | 90 | | |
| | | | | | | 120→110 | 9 | | |
| 8 | 1.005 | 0.018 | 450 | 5.23 | 151 | 95→100 | 10 | 95 to <110 | 213 |
| | | | | | | 100 | 180 | | |
| | | | | | | 100→110 | 23 | | |
| | | | | | | 110 | 30 | 110-125 | 114 |
| | | | | | | 110→120 | 15 | | |
| | | | | | | 120 | 60 | | |
| | | | | | | 120→110 | 9 | | |
| 9 | 1.005 | 0.018 | 450 | 5.23 | 151 | 95→100 | 11 | 95 to <110 | 218 |
| | | | | | | 100 | 180 | | |
| | | | | | | 100→110 | 27 | | |
| | | | | | | 110 | 30 | 110-125 | 117 |
| | | | | | | 110→120 | 16 | | |
| | | | | | | 120 | 60 | | |
| | | | | | | 120→110 | 11 | | |
| 10 | 1.005 | 0.018 | 450 | 5.23 | 151 | 95→100 | 9 | 95 to <110 | 214 |
| | | | | | | 100 | 180 | | |
| | | | | | | 100→110 | 25 | | |
| | | | | | | 110 | 30 | 110-125 | 117 |
| | | | | | | 110→120 | 16 | | |
| | | | | | | 120 | 60 | | |
| | | | | | | 120→110 | 11 | | |
| 11 | 0.955 | 0.0171 | 385 | 4.48 | 151 | 95→100 | 9 | 95 to <110 | 211 |
| | | | | | | 100 | 180 | | |
| | | | | | | 100→110 | 22 | | |
| | | | | | | 110 | 30 | 110-125 | 116 |
| | | | | | | 110→120 | 16 | | |
| | | | | | | 120 | 60 | | |
| | | | | | | 120→110 | 11 | | |

| | Preparation of Catalyst | | | |
|---|---|---|---|---|
| | Additive | | Molar Ratio, Choline Chloride/Iron | |
| Example | Kind | (mol) | (mol/mol) | Remarks |
| 6 | TEOA | 0.018 | 1.0 | Homogeneous dissolution |
| | MAA | 0.71 | | |
| | Choline chloride | 0.018 | | |
| | Water | 0.0466 | | |
| 7 | TEOA | 0.018 | 1.0 | Homogeneous dissolution |
| | MAA | 0.71 | | |
| | Choline chloride | 0.018 | | |
| | Water | 0.0466 | | |
| 8 | TEOA | 0.020 | 1.1 | Homogeneous dissolution |
| | MAA | 0.71 | | |
| | Choline chloride | 0.020 | | |
| | Water | 0.0517 | | |

TABLE 2-continued

| | | | | | |
|---|---|---|---|---|---|
| 9 | TEOA | 0.018 | | 1.7 | Homogeneous dissolution |
| | MAA | 0.71 | | | |
| | Choline chloride | 0.031 | | | |
| | Water | 0.0803 | | | |
| 10 | TEOA | 0.018 | | 0.4 | Homogeneous dissolution |
| | MAA | 0.71 | | | |
| | Choline chloride | 0.0072 | | | |
| | Water | 0.0186 | | | |
| 11 | TEOA | 0.0294 | | 1.1 | Homogeneous dissolution |
| | MAA | 1.47 | | | |
| | TBACl | 0.0189 | | | |

TBACl: Tetrabutylammonium chloride

Iron Powder: *) was an atomized iron powder (180 μm, surface oxygen content: 2.1% by mass) manufactured by Wako Pure Chemical Industries Ltd., and the others were an electrolytic iron powder (150 μm, surface oxygen content: 2.1% by mass) manufactured by Wako Pure Chemical Industries, Ltd.

TABLE 3

| | Preparation of Catalyst | | | | | | | | |
|---|---|---|---|---|---|---|---|---|---|
| Comparative Example | Iron Powder (g) | MAA (g) | MAA (mol) | Moisture Content in MMA (ppm) | Preparation Temperature (°C.) | Preparation Time (min) | Preparation Temperature Range (°C.) | Preparation Time (min) | |
| 1 | 1.117 | 0.020 | 450 | 5.23 | 151 | 90 | 600 | <95 | 600 |
| 2 | 1.117 | 0.020 | 450 | 5.23 | 151 | 95→110 | 19 | 95 to <110 | 19 |
| | | | | | | 110→125 | 13 | 110-125 | 13 |
| | | | | | | 125→130 | 4 | >125 | 609 |
| | | | | | | 130 | 600 | | |
| | | | | | | 130→125 | 5 | | |
| 3 | 1.005 | 0.018 | 450 | 5.23 | 151 | 95→100 | 22 | 95 to <110 | 22 |
| | | | | | | 110 | 300 | 110-125 | 300 |
| 4 | 1.005 | 0.018 | 450 | 5.23 | 151 | 95→100 | 11 | 95 to <110 | 93 |
| | | | | | | 100 | 60 | | |
| | | | | | | 100→110 | 22 | | |
| | | | | | | 110 | 60 | 110-125 | 172 |
| | | | | | | 110→120 | 12 | | |
| | | | | | | 120 | 90 | | |
| | | | | | | 120→110 | 10 | | |
| 5 | 1.117 | 0.020 | 450 | 5.23 | 151 | 95→100 | 28 | 95 to <110 | 28 |
| | | | | | | 110→125 | 20 | 110-125 | 20 |
| | | | | | | 125→130 | 9 | >125 | 189 |
| | | | | | | 130 | 180 | | |
| | | | | | | 130→125 | 5 | | |
| | | | | | | 125→110 | 9 | 110-125 | 9 |
| 6 | 1.117 | 0.020 | 450 | 5.23 | 151 | 95→100 | 18 | 95 to <110 | 98 |
| | | | | | | 100 | 80 | | |

| | Preparation of Catalyst | | | |
|---|---|---|---|---|
| Comparative Example | Additive Kind | (mol) | Molar Ratio, Choline Chloride/Iron (mol/mol) | Remarks |
| 1 | — | — | — | Not dissolved |
| 2 | — | — | — | Partially polymerized |
| 3 | TEOA | 0.018 | 1.0 | Homogeneous dissolution |
| | MAA | 0.71 | | |
| | Choline chloride | 0.018 | | |
| | Water | 0.0466 | | |
| 4 | TEOA | 0.018 | 1.0 | Homogeneous dissolution |
| | MAA | 0.71 | | |
| | Choline chloride | 0.018 | | |
| | Water | 0.0466 | | |
| 5 | TEOA | 0.010 | 0.5 | Homogeneous dissolution |
| | MAA | 0.71 | | |
| | Choline chloride | 0.010 | | |
| | Water | 0.0259 | | |
| 6 | — | — | — | Not dissolved |

TABLE 4

| | EO Amount | | | | Reaction Results | | | |
|---|---|---|---|---|---|---|---|---|
| | Dropping Amount of 30° C. for | Dropping Amount of 66° C. for | Total | | Reaction Yield | Amount of Ethylene Glycol Dimethacrylate | Amount of Diethylene Glycol Monomethacrylate | Presence/ Absence of solid |
| | 7 min (g) | 120 min (g) | (g) | (mol) | (%) | (mass %) | (mass %) | deposition |
| Example 1-1 | 29.1 | 280.9 | 310 | 7.037 | 89.5 | 0.07 | 4.10 | Absence |
| Example 1-2 | 29.3 | 270.7 | 300 | 6.810 | 89.3 | 0.05 | 3.83 | Absence |
| Example 2 | 29.3 | 305.7 | 335 | 7.605 | 90.0 | 0.08 | 3.83 | Absence |
| Example 3 | 27.6 | 282.4 | 310 | 7.037 | 89.7 | 0.07 | 3.94 | Absence |
| Example 4 | 28.3 | 301.7 | 330 | 7.491 | 89.4 | 0.06 | 4.00 | Absence |
| Example 5 | 30.1 | 299.9 | 330 | 7.491 | 85.8 | 0.06 | 3.86 | Absence |
| Example 6 | 28.8 | 271.2 | 300 | 6.810 | 88.2 | 0.07 | 3.90 | Absence |
| Example 7 | 29.5 | 295.5 | 325 | 7.378 | 86.3 | 0.06 | 3.80 | Absence |
| Example 8 | 29.0 | 296.0 | 325 | 7.378 | 89.4 | 0.07 | 3.84 | Absence |
| Example 9 | 27.9 | 302.1 | 330 | 7.491 | 88.2 | 0.52 | 3.13 | Absence |
| Example 10 | 28.1 | 291.9 | 320 | 7.264 | 88.5 | 0.04 | 4.47 | Absence |
| Example 11 | 27.8 | 297.2 | 325 | 7.605 | 93.3 | 0.09 | 3.62 | Absence |
| Comparative Example 1 | — | — | — | — | — | — | — | — |
| Comparative Example 2 | — | — | — | — | — | — | — | — |
| Comparative Example 3 | 28.5 | 296.5 | 325 | 7.378 | 88.0 | 0.07 | 4.50 | Absence |
| Comparative Example 4 | 27.9 | 302.1 | 330 | 7.491 | 85.4 | 0.07 | 4.74 | Absence |
| Comparative Example 5 | 29.8 | 310.2 | 340 | 7.719 | 84.9 | 0.24 | 8.91 | Absence |
| Comparative Example 6 | — | — | — | — | — | — | — | — |

TABLE 5

| | Kind and Maker Name of Iron Powder | Results of XRF Analysis (%) | | | Solubility Time after 120° C. was reached | | | | Remarks |
|---|---|---|---|---|---|---|---|---|---|
| | | C | O | Fe | 60 min | 120 min | 180 min | 240 min | |
| Example 2 | Electrolytic iron powder Wako Pure Chemical Industries, Ltd. | 2.5 | 2.1 | 95.2 | ○ | | | | |
| Example 12 | Electrolytic iron powder 2 Wako Pure Chemical Industries, Ltd. | 1.3 | 1.1 | 97.6 | X | X | ○ | | |
| Example 13 | Atomized iron powder Wako Pure Chemical Industries, Ltd. | 2.5 | 2.1 | 95.0 | ○ | | | | |
| Comparative Example 7 | Guaranteed iron powder Kishida Chemical Co., Ltd. | 1.9 | 7.3 | 90.7 | X | X | X | X | Undissolved remain was present |
| Example 14 | JIP 255M JFE Steel Corp. | 3.6 | 2.4 | 93.5 | ○ | | | | |
| Example 15 | JIP 255M-7C JFE Steel Corp. | 2.1 | 2.1 | 95.3 | ○ | | | | |
| Comparative Example 8 | JIP NNF-10 JFE Steel Corp. | 3.7 | 6.2 | 89.7 | X | X | X | X | Undissolved remain was present |

○: Dissolved, homogeneous red solution
X: Not dissolved

INDUSTRIAL APPLICABILITY

The use of the method according to the present invention can provide iron methacrylate suitable as a catalyst for production of a hydroxyalkyl methacrylate excellent in activity, selectivity and solubility by using an inexpensive and non-corrosive metallic iron as a raw material.

The invention claimed is:

1. A method for producing iron methacrylate, the method comprising subjecting a mixture of a metallic iron and methacrylic acid to a heat treatment at a temperature of from 95° C. to 110° C. for 100 to 600 min,
   wherein the metallic iron has an oxygen atom content by XRF analysis of a surface thereof of 6% by mass or lower.

2. The method of claim 1, further comprising:
   subjecting the mixture, after the heat treatment, to a further heat treatment at a temperature of from 110° C. to 125° C. for 30 to 300 min, and
   subsequently cooling to 100° C. or lower.

3. A method for producing a hydroxyalkyl methacrylate the method comprising reacting an alkylene oxide with a methacrylic acid and the iron methacrylate of claim 1,
   wherein the iron methacrylate is a catalyst.

4. The method of claim 3, further comprising reacting with a quaternary ammonium salt and an amine compound,
   wherein the quaternary ammonium salt and amine compound are catalysts.

5. The method of claim 4, wherein the quaternary ammonium salt is in an amount of from 0.5 to 1.5 mol with respect to 1 mol of the iron methacrylate.

6. A method for producing a hydroxyalkyl methacrylate, the method comprising reacting an alkylene oxide with a methacrylic acid and the iron methacrylate of claim 2,
   wherein the iron methacrylate is a catalyst.

7. The method of claim 6, further comprising reacting with a quaternary ammonium salt and an amine compound,
   wherein the quaternary ammonium salt and amine compound are catalysts.

8. The method of claim 7, wherein the quaternary ammonium salt is in an amount of from 0.5 to 1.5 mol with respect to 1 mol of the iron methacrylate.

9. The method of claim 1, wherein the metallic iron is an iron powder.

10. The method of claim 9, wherein a particle diameter of the iron powder is of from 10 to 500 μm.

11. The method of claim 9, wherein a particle diameter of the iron powder is of from 60 to 300 μm.

12. The method of claim 1, wherein the metallic iron has an oxygen atom content by XRF analysis of a surface thereof of 3% by mass or lower.

13. The method of claim 1, wherein the metallic iron has an oxygen atom content by XRF analysis of a surface thereof is of from 0% to 6% by mass.

14. The method of claim 1, wherein the metallic iron has an oxygen atom content by XRF analysis of a surface thereof is of from 1% to 6% by mass.

15. The method of claim 1, wherein the metallic iron has an oxygen atom content by XRF analysis of a surface thereof is of from 1.5% to 6% by mass.

16. The method of claim 1, wherein the heat treatment is at a temperature of from 95° C. to 105° C.

17. The method of claim 1, wherein the heat treatment is carried out for 150 to 500 min.

18. The method of claim 1, wherein the heat treatment is carried out for 200 to 400 min.

19. The method of claim 1, wherein an amount of moisture of the methacrylic acid is 300 ppm or smaller.

20. The method of claim 1, wherein an amount of moisture of the methacrylic acid is 200 ppm or smaller.

* * * * *